US006268481B1

(12) United States Patent
Morjana

(10) Patent No.: US 6,268,481 B1
(45) Date of Patent: Jul. 31, 2001

(54) COVALENTLY COUPLED TROPONIN COMPLEXES

(75) Inventor: Nihmat Morjana, Pembroke Pines, FL (US)

(73) Assignee: Medical Analysis Systems, Inc., Camarillo, CA (US)

( * ) Notice: Subject to any disclaimer, the term of this patent is extended or adjusted under 35 U.S.C. 154(b) by 0 days.

(21) Appl. No.: 08/898,649

(22) Filed: Jul. 22, 1997

Related U.S. Application Data

(63) Continuation-in-part of application No. 08/865,468, filed on May 29, 1997.

(51) Int. Cl.[7] .................................................. A61K 31/00
(52) U.S. Cl. .............................. 530/350; 560/841; 436/86; 436/811; 514/12
(58) Field of Search ...................... 530/350, 841; 436/86, 811; 514/12

(56) References Cited

U.S. PATENT DOCUMENTS

| 3,466,249 | 9/1969 | Anderson | 252/408 |
|---|---|---|---|
| 3,629,142 | 12/1971 | Marbach | 252/408 |
| 3,682,835 | 8/1972 | Louderback | 252/408 |
| 3,876,375 | 4/1975 | Maurukas | 23/230 B |
| 3,897,363 | 7/1975 | Louderback et al. | 252/408 |
| 4,105,499 | 8/1978 | Kiyasu | 195/103.5 R |
| 4,121,905 | 10/1978 | Maurukas | 23/230 B |
| 4,189,401 | 2/1980 | Louderback | 252/408 |
| 4,264,471 | 4/1981 | Briggs | 252/408 |
| 4,271,122 | 6/1981 | Strässle et al. | 422/61 |
| 4,276,376 | 6/1981 | Hundt et al. | 435/17 |
| 4,324,685 | 4/1982 | Louderback | 252/408 |
| 4,324,687 | 4/1982 | Louderback et al. | 252/408 |
| 4,438,202 | 3/1984 | Engler et al. | 436/8 |
| 4,476,224 | 10/1984 | Adler | 435/253 |
| 4,626,511 | 12/1986 | Artiss et al. | 436/8 |
| 4,643,976 | 2/1987 | Hoskins | 436/15 |
| 4,678,754 | 7/1987 | Hoskins | 436/15 |
| 4,703,013 | 10/1987 | Louderback et al. | 436/12 |
| 4,767,843 | 8/1988 | Yazaki et al. | 530/387 |
| 4,879,216 | 11/1989 | Hallermayer et al. | 435/7 |
| 4,943,427 | 7/1990 | Yazaki et al. | 424/1.1 |
| 4,994,375 | 2/1991 | Posner et al. | 435/7 |
| 4,996,073 | 2/1991 | Copeland | 426/487 |
| 5,028,542 | 7/1991 | Kennamer et al. | 436/14 |
| 5,132,230 | 7/1992 | Rosenthal et al. | 436/15 |
| 5,206,007 | 4/1993 | Ooshima et al. | 424/9 |
| 5,217,890 | 6/1993 | Daggett | 435/188 |
| 5,227,307 | 7/1993 | Bar Or et al. | 436/63 |
| 5,240,853 | 8/1993 | Copeland | 435/262 |
| 5,266,488 | 11/1993 | Ordahl et al. | 435/240.2 |
| 5,290,519 | 3/1994 | Bar Or et al. | 422/61 |
| 5,290,678 | 3/1994 | Jackowski | 435/7.4 |
| 5,296,377 | 3/1994 | Rapkin et al. | 436/13 |
| 5,418,139 | 5/1995 | Campbell | 435/7.21 |
| 5,449,669 | 9/1995 | Metcalfe et al. | 514/13 |
| 5,498,524 | 3/1996 | Hall | 435/7.1 |
| 5,560,937 | 10/1996 | Lee et al. | 424/569 |
| 5,583,200 | 12/1996 | LaRue et al. | 530/350 |
| 5,604,105 | 2/1997 | Jackowski | 435/7.4 |
| 5,837,680 | * 11/1998 | Moses et al. | 514/12 |

FOREIGN PATENT DOCUMENTS

| 0 743 522 A1 | 11/1996 | (EP) . |
|---|---|---|
| 0 752 426 A2 | 1/1997 | (EP) . |
| 2200358A | 1/1987 | (GB) . |
| 2275774A | 2/1994 | (GB) . |
| WO 9415217 | 7/1994 | (WO) . |
| WO 94 27156 | 11/1994 | (WO) . |
| WO 9427156 | 11/1994 | (WO) . |
| WO 9610076 | 4/1996 | (WO) . |
| WO 96/27661 | 9/1996 | (WO) . |
| WO 9632648 | 10/1996 | (WO) . |
| WO 97/19955 | 6/1997 | (WO) . |

OTHER PUBLICATIONS

Chong et al., *J. Biol. Chem.*, 257(19), 11667–72, 1982.*

Sutoh et al., *Biochemistry*, 19(16), 3878–82, 1980.*

Katrakha et al., Clin. Chem. (Washington D.C.), 43(8, Pt. 1), 1379–1385, 1997.*

Cummins, et al., "Immunoassay of the cardiac–specific isoform of troponin–1 in the diagnosis of heart muscle damage," *Biochemical Society Transactions*, 622nd Meeting, Leicester, 15(6):1060–1061 (1987).

Gao, et al., "Role of troponin I proteolysis in the pathogenesis of stunned myocardum," *Cir. Res.*, 80(3):393–399 (1997).

Kobayashi, et.al., "Extensive interactions between troponins C and I. Zero–length cross–linking of troponin I and acetylated troponin C," *Biochem.*, 34: 10946–10952 (1995).

Leszyk, et al., "Cross–linking of Rabbit Skeletal Muscle Troponin Subunits: Labeling of Cysteine–98 of Troponin C with 4–Maleimidobenzophenone and Analysis of Products Formed in the Binary Complex with Troponin T and Ternary Complex with Troponins I and T," *Biochem.*, 27: 6983–6987 ( 1988).

Morjana, et al., "Biochemical and immunological properties of a cyanogen bromide fragment of human cardiac troponin I," *FASEB J.*, 10(6): A–1295 (1996).

Farah, et al., "The troponin complex and regulation of muscle contraction," *The FASEB J.*, 9: 756–767 (1995).

Morjana, et al., "Cardiac troponin I exists as a complex in patient serum," *Clin. Chem.*, 43(6):S157 (1997).

(List continued on next page.)

*Primary Examiner*—Dwayne C. Jones
*Assistant Examiner*—C. Delacroix-Muirheid
(74) *Attorney, Agent, or Firm*—Morrison & Foerster LLP

(57) ABSTRACT

Stabilized compositions for use in clinical assays for troponin are disclosed. The compositions are covalently coupled complexes of cardiac troponin I, cardiac troponin T, and/or troponin C.

7 Claims, 7 Drawing Sheets

OTHER PUBLICATIONS

Morjana, et al., "Degradation of human cardiac troponin I after myocardial infraction," *The FASEB J.*, 2(9):A998 (1997).

Access® Immunoassay System Package Insert for Troponin I ©1995 Revised Dec. 1996.

Grabarek, Zenon, "Properties of Troponin C Acetylated at Lysine Residues" Biochemistry (34) 11872–11881 (1995).

Pan, Bo–Sheng and Potter, James D. "Two Genetically Expressed troponin T Fragments Representing α and β Isoforms Exhibit Functional Differences" Amer. Soc. Of Biochemistry and Molecular Biology (267) 23052–23056 Nov. 1993.

Farah, et al. "The Troponin Complex and Regulation of Muscle Contraction" FASEB (9) Jun. 1995.

Schaertl, S. et al. "Separation and Characterization of the Two Functional Regions of Troponin Involved in Muscle Thin Filament Regulation" Biochemistry (34) 15890–15894 (1995).

Ramakrishnan, Sundaram et al. "Investigation f the Structural Requirements of the Troponin C Central Helix for Function" Biochemistry (34) 16789–16796 (1995).

Dahiya, Ranjan "Equilibrium Linkage Analysis of Cardiac Thin Filament Assembly" Journal of Biological Chemistry (269) (47) 29457–29461 1994.

Potter, James et al. "A Direct Regulatory Role of Troponin T and a Dual Role for Troponin C in the Ca 2+ Regulation of Muscle Contraction" Journal of Biological Chemistry (270) (6) 2557–2562 1995.

Fisher, Donald et al. "NH2–terminal Truncation of Skeletal Muscle Troponin T Does not Alter the Ca 2+ Sensitivity of Thin Filament Assembly" Journal of Biological Chemistry (270) (43) 25455–25460 (1995).

Morjana, NA et al. "Cardiac Troponin I Exists as a Complex in Patient Serum" Abstract 229 Clinical Chemistry (43) (6) S157 1997.

Ohman, E. Magnus et al. "Cardiac Troponin T Levels for Risk Stratification in Acute Myocardial Ischemia" New England Journal of Medicine, (335) (18) 1333–1341 1996.

Antmann, Elliot M. et al. "Cardiac Specific Troponin I Levels to Predict the Risk of Mortality in Patients with Acute Coronary Syndromes" New England Journal of Medicine, (335) (18) 1342–1388 1996.

Wong, Shan S. "Chemistry of Protein Conjugation and Cross–Linking" CRC Press.

Bodor et al. "Development of Monoclonal Antibodies for an Assay of Cardiac Troponin I and Preliminary Results in Suspected Cases of Myocardial Infarction" Clinical Chemistry (38) (11) 2203–2214 (1992).

Jacobson, K. Bruce et al. "Partial Purification of an Oxygen Scavenging Cell Membrane Fraction for Use in Anaerobic Biochemical Reactions" Biotechnology and Applied Biochemistry (9) 368–379 (1987).

Armour, KL "Cloning and Expression in *Escherichia coli* of the cDNA encoding human cardiac troponin I" Gene (131) (2) 287–292 (1993).

Kobayashi et al., "Structure of the Troponin Complex: Implication of photocross–linking of troponin I to troponin C thiol mutants" Journal of Biological Chemistry (269) 5725–5729 (1994).

Leszyk et al. "Cross–Linking of rabbit skeletal muscle troponin with the photoactive reagent . . . " Biochemistry (26) 7042–7047 (1987).

Larue et al. "New Monoclonal Antibodies as Probes for human Cardiac Troponin I" Molecular Immunology (29), No. 2, 271–178, (1992).

Adams, J. et al. "Cardiac troponin I, A marker with High Specificity for Cardiac Injury" Circulation, vol. 88 No. 1, 100–106 (Jul. 1993).

Apple, F.S., Diagnostic markers for Detection of Acute Myocardial Infarction and Reperfusion, Laboratory Medicine vol. 23, No. 5 297–302 (May 1992).

Berson, G. et al. Pflugers Arch. 374: 277–283 (1978).

Burtnick, L.D. et al. Can. J. Biochem. 53: 1207–1213 (1975).

Cheung, H. et al. "Interactions of Troponin Subunits: Free Energy of Binary and Ternary Complexes" Biochemistry (26) (18) 1987.

Cummins, P. et al. Biochem J. 171: 251–259 (1978).

Cummins, B. et al., Am. Heart J. 113 (6): 1333–1344 (1987).

F. Di Lisa, et al. Specific Degradation of troponin T and I by μ–calpain and its Modulation by Substrate Phosphorylation, Biochm. J. (1995) 308 57–61.

Fujita–Becker, S. et al. "Reconstitution of Rabbit Skeletal Muscle Troponin from the recombinant Subunits All Expressed in and Purified from *E. coli*" J. Biochem, 114. 438–444 (1993).

Grabarek, Z. et al. "Proteolytic Fragments of troponin C" Journal of Biol. Chem. vol. 256 No. 24 13121–13127 (1981).

Greaser, M. et al. "Reconstitution of Troponin Activity from Three Protein Components" Journal of Biol. Chem. vol. 246 (13) 4226–4233 (1971).

Greaser, M. et al. "Purification and properties of the Components from Troponin" Journal of Biol. Chem. vol. 248 (6) 2125–2133 (1973).

Guo, X. et al. "Mutagenesis of Cardiac Troponin I" Journal of Biol. Chem. vol. 269 (21) 15210–15216 (1994).

Hastings, K.E.M., et al. J. Biol. Chem. 266 (29) 19659019665 (1991).

Katus, H. et al. "Proteins of the Troponin Complex" Laboratory Medicine, vol. 23 (5) 1992.

Ladenson, J. et al. "Development and Characterization of Monoclonal Antibodies Specific to Troponin" Abstract International Congress of Clinical Chemistry.

Malnic, et al. "Assembly of functional skeletal muscle troponin complex in *Escherichia coli*" J. Biochem. 222 49–54 (1994).

Morjana, N. et al. The Reversible Denaturation of Cardiac Troponin I, FASEB Journal, Abstract 1232 vol. 9 No. 6 (1995).

Morjana, N. et al. "The Biochemical and Immunological Properties of a Cyanogen Bromide Fragment of Human Cardiac Troponin I" FASEB Journal, Abstract 1706 vol. 10 No. 6 (1996).

Ojima, t. et al. "Amino Acid Sequence of C–Terminal 17 kDa CNBr–Fragment of Akazara Scallop Troponin I" J. Biochem. 117 158–162 (1995).

Ottlinger, M. et al. "Troponin T and Troponin I: New Serum Markers of Myocardial Damage." CLN, Jul. 1994.

Panteghini, M. "Cardiac Myosin Light Chains", Laboratory Medicine, vol. 23 No. 5318–5322 (1992).

Potter, J.D., "Preparation of Troponin and Its Submits [sic]" Methods in Enzymology, vol. 85: 241–263 (1982).

Potter, J.D., et al. "The Regulation of Cardiac Muscle Contraction by Troponin" Cell Motility and Muscle, vol. 2 245–255 (1982).

Reinach, F. "Cloning Expression, and Site–directed Mutagenesis of Chicken Skeletal Muscle Troponin C" Journal of Biological Chem. vol. 263 (5) 2371–2376 (1988).

Sheng, Z. et al. "Isolation, Expression, and Mutation of a Rabbit Skeletal Muscle cDNA Clone for Troponin I" The Journal of Biol. Chem. vol. 267 (35) 25407–25413 (1992).

Swenson, C. et al. "Interaction of Troponin C and Troponin C Fragments with Troponin I and the Troponin I Inhibitory Peptide" Biochem. vol. 31 (13) 3420–3429 (1992).

Syska, H. et al. Biochem J. 153 (2) 375–387 (1976).

Trinquier, S. "Highly Specific Immunoassay for Cardiac Troponin I Assessed in Noninfarct Patients with Chronic Renal Failure or Severe Polytrauma" Clinical Chemistry vol. 41 (11) (1995)I.

Tsuchida, K. et al. "Degradation of Myocardial Structural Proteins in Myocardial Infarcted Dogs is Reduced by Ep459 a Cysteine Proteinase Inhibitor" Biol. Chem. Hoppe–Seyler vol. 367 39–45 (1986).

Vaidya, H.C. "Myoglobin" Laboratory Medicine vol. 23 (5) (1992).

Vallins, W.J. et al. FEBS Letters 270 (1,2): 57–61 (1990).

Whipple, G. et al., "Degradation of Myofibrillar Proteins by Extractable Lysosomal Enzymes and m–Caipain and the Effects of Zinc Chloride" J. Anim. Sci. 69:4469–4460 (1991).

Wilkinson, J.M. et al, Nature, 271:31–35 (1978).

Wu, A.H. et al., "Cardiac Troponin T Immunoassay for Diagnosis of Acute Myocardial Infarction" Clinical Chem. vol. 40 (6) 900–907 (1994).

Zot A. et al. "Structural Aspects of Troponin– Tropomyosin Regulation of Skeletal Muscle contraction" Ann. Rev. Biophys. Chem. vol. 16 1535–1559 (1987).

Leszyk, John et al. "Characterization of Zero–Length Cross–Links between Rabbit Skeletal Muscle Troponin C and Troponin I: Evidence of Direct Interaction between the Inhibitory Region of Troponin I and the $NH_2$–Terminal, Regulatory Domain of Troponin C" Biochemistry (29) 299–304 (1990).

Kobayashi, Tomoyoshi et al. "Extensive Interactions between Troponins C and I Zero–Length Cross–Linking of Troponin I and Acetylated Troponin C" Biochemistry (34) 10946–10952 (1995).

* cited by examiner

```
        -7           -1 0 1
(r)   M-A-S-M-T-L-W-M-A-D-G-S-S-D-A-A-R-E-P-R-P-A-P-A-P-    SEQ ID NO. 1
(h)                   A-D-G-S-S-D-A-A-R-E-P-R-P-A-P-A-P-    SEQ ID NO. 2

SEQ ID:3

A-D-G-S-S-D-A-A-R-E-P-R-P-A-P-A-P-I-R-R-R-S-S-N-Y-R-A-Y-A-
T-E-P-H-A-K-K-K-S-K-I-S-A-S-R-K-L-Q-L-K-T-L-L-L-Q-I-A-K-Q-
E-L-E-R-E-A-E-E-R-R-G-E-K-G-R-A-L-S-T-R-C*-Q-P-L-E-L-T-G-L-
G-F-A-E-L-Q-D-L-C*-R-Q-L-H-A-R-V-D-K-V-D-E-E-R-Y-D-I-E-A-K-
V-T-K-N-I-T-E-I-A-D-L-T-Q-K-I-F-D-L-R-G-K-F-K-R-P-T-L-R-R-
V-R-I-S-A-D-A-M c*=(cam)=S-carboxyamidomethylcysteine

FIG. 2

Lane: 2 3 4 5 6 7 8

COVALENTLY COUPLED TROPONIN COMPLEXES

CROSS-REFERENCES TO RELATED APPLICATIONS

This application is a continuation-in-part of U.S. Ser. No. 08/865,468, filed May 29, 1997.

FIELD OF INVENTION

The present invention relates generally to clinical chemistry. In particular, it relates to stabilized troponin complexes useful in the diagnosis of myocardial infarction or other ischemic events.

BACKGROUND OF THE INVENTION

The determination of the presence or amount of certain constituents or analytes is useful in the diagnosis of disease and physical well-being. Compositions which behave similarly to how constituents present in human bodily fluids (e.g. blood, blood serum, plasma, spinal fluid or urine) behave are used in clinical laboratories. These compositions assist in the determination of whether the clinical instrumentation and procedures used by the laboratory to measure the constituents are accurate. These compositions are also used to calibrate the clinical devices which measure the amount or presence of the constituent in a sample. These compositions will be referred to hereinafter as control compositions or controls.

In addition, it is important that the analyte or analyte analog present in the control composition behave similarly to the corresponding analyte to be tested for in a patient's bodily fluid—that is, the control composition should mimic the patient sample.

Rapid and simple tests that can be used to accurately diagnose the occurrence of myocardial infarction ("MI") or distinguish other ischemic events such as unstable angina are extremely important. Cardiac troponin I (cTnI) and troponin T have recently become established as the markers of choice in evaluating cardiac distress. See, New England Journal of Medicine Volume 335 No. 18, pages 1342–1349, Antman et al. and pages 1333–1341, Ohman et al.

The Troponin complex is present in both skeletal and cardiac muscles and consists of three subunits, Troponin T ("TnT") the tropomyosin binding subunit, Troponin C ("TnC"), the $Ca^{++}$ binding subunit and TnI, which inhibits the actomyosin $Mg^{++}$-ATPase.

The majority of the research into the troponin complex has centered around the regulatory function and structure of the troponin complex in skeletal muscle. The troponin complex assists in muscle contraction. The TnC molecule has four binding domains to bind divalent metal ions. The $Ca^{++}/Mg^{++}$ binding sites are in the COOH terminal region and the $Ca^{++}$ binding sites are in the amino terminal region. In studies of skeletal muscle, in the absence of $Ca^{++}$, the amino terminus of TnI binds to the COOH terminus region of TnC and to the globular COOH terminus region of TnT. Thus, research indicates that TnI and TnC are anti-parallel and TnI and TnT are anti-parallel. The presence of calcium ion increases the TnC amino terminus domain's affinity for the inhibitory and COOH regions of TnI. In addition, there is a hydrophobic surface in the N-terminal domain of TnC that represents a $Ca^{++}$ dependent binding site for TnI and TnT. It has been proposed that the $Ca^{++}$ dependent reactions relate to the regulatory mechanism and $Ca^{++}$ independent interactions maintain the structural integrity of the complex.

In order to study structure and function of the troponin complex in its regulation of skeletal muscle, cross-linking studies have been accomplished. See, Farah, C. and Reinach, F. Review: The Troponin complex and regulation of muscle contraction. FASEB Journal 9 pp. 755–767 (1995). Covalent binding between TnC and skeletal muscle TnI has been formed between the carboxyl groups in the TnC and lysine groups in TnI using EDC. Kobayoshi et al. (1994), Structure of the troponin complex: implications of photocross-linking of troponin I to troponin C thiol mutants. J. Biol. Chem. 269, 5725–5729. In addition Leszyk et al. (1987) Cross-linking of rabbit skeletal muscle troponin with the photoactive reagent 4-malemidobenzophenone; identification of residues in troponin I that are close to cystein-98 of troponin C. Biochemistry 26, 7042–7047, reported that the main product of cross-linking between TnC and skeletal muscle TnI comprises segments derived from the N-terminal regulatory domain of TnC (residues 46 to 78) and the inhibitory region of skeletal TnI (residues 96–116). The Troponin complex is also referred to herein as the ternary complex.

U.S. Ser. No. 08/865,468, filed on May 29, 1997 and also owned by applicant, discloses that it had been discovered that the majority of native cTnI in human serum after an MI is associated with TnC and TnT. The presence of TnI in a complex with other troponin subunits in MI patient serum increases its stability and protects it from further degradation. In addition the troponin complex protects the sites where cardiac-specific antibodies bind. U.S. Ser. No. 08/865,468, filed on May 29, 1997 also discloses methods to isolate the complex from MI patient serum.

The cardiac isotype of the myofibrillar contractile protein, Troponin I ("TnI"), is uniquely located in cardiac muscle. TnI is the inhibitory sub-unit of Troponin, a thin filament regulatory protein complex, which confers calcium sensitivity to the cardiac and striated muscle. Troponin I exists in three isoforms: two skeletal TnI (fast and slow) isoforms (Molecular Weight=19,800 daltons) and a cardiac TnI ("cTnI") isoform with an additional 31 residues (human TnI) on the N-terminus resulting in a molecular weight of 23,000 daltons.

Cardiac TnI is found in human serum rapidly (within approximately 4 to 6 hours) following an MI. It reaches a peak level after approximately 18–24 hours and remains at elevated levels in the blood stream for up to 6 to 7 days. Thus, immunoassays which can test for human cTnI are valuable to the medical community and to the public.

It is desirable to use an immunologically reactive human cTnI isoform comparable to that found in MI patient serum. We found that MI patient serum contains TnI fragment(s) which is the result of the C-terminal processing of cTnI molecule. The high sequence homology found in the C-terminal region between cardiac TnI and skeletal muscle TnI (Larue et al. 1992 Molec. Immunology 29, 271–278, Vallins et al. 1990 FEBS Lett. 270, 57–61, Leszky et al. 1988 Biochemistry 27, 2821–2827) produce TnI antibodies directed against this region having non-cardiac specificity (Larue et al. 1992). Our data and Larue et al. 1992 suggest that most of the known cTnI specific antibodies have their epitopes located approximately in the first 75% of the TnI molecule. Therefore, this portion of the TnI molecule should function as a MI specific cTnI isoform in most immunoassay systems.

Currently cTnI immunoassays are commercially available from Dade International, Behring Diagnostics, and Sanofi Pasteur Diagnostics. The Dade product is the StratusO Cardiac Troponin-I assay.

Native intact human cTnI is difficult to obtain because of the scarcity of human heart and native intact human cTnI is highly subject to proteolytic degradation during purification. Recombinant cardiac TnI ("r-TnI"), unlike the native human cTnI, can be produced and purified in acceptable quantities. As expressed by Dade, the primary structure of r-TnI contains 226 amino acids (SEQ ID NO: 1); 209 of them represent the TnI sequence (SEQ ID NO: 2). In addition to the primary sequence of cTnI (SEQ ID NO: 2), r-TnI, as expressed by Dade International, has a leading sequence of 8 amino acids (MASMTLWM) on the N-terminal, and a tail sequence of 9 amino acids (PMVHHHHHH) on the C-terminal (SEQ ID NO: 1). The primary structure of the r-TnI molecule has methionine residues at positions −7, −4, 0, 153, 154, 200 and 211 (SEQ ID NO: 1). See also FIG. 1.

Full length cardiac troponin I is known to have the following sequence:
ADGSSDAAREPRPAPAPIRRRSSNYRAYATEPHAKK-KSKISASRKLQLKTLLLQIAKQELEREAEERRGEK-GRALSTRCQPLELTGLGFAELQDLCRQLHARVDK-VDEERYDIEAKVTKNITEIADLTQKIFDLRGKFKR-PTLRRVRISADAMMQALLGARAKESLDLRAHLK-VKKEDTEKENREVGDWRKNIDALSGMEGRKK-KFES (SEQ ID NO: 2) (Armour, K. L. et al.,(1993) Cloning and Expression in *Escheria Coli* of the cDNA Encoding Human Cardiac Troponin I, Gene, 131 (2):287–292).

U.S. Ser. No. 08/564,526, also owned by applicants, and incorporated herein by reference, discloses the use of a human cTnI fragment generated from human r-TnI by chemical cleavage. The cleavage of r-TnI by cyanogen bromide (CNBr) results in a major polypeptide of 153 amino acids, hereinafter referred to as the "ICNBr-cTnI isoform" (SEQ ID NO: 3). See FIG. 2. The CNBr-cTnI isoform represents 73% of the primary structure of human cTnI and is immunologically more reactive than r-TnI. The purified CNBr-cTnI isoform has an average of 3–4 times more reactivity than r-TnI and lower non-specific binding, as measured by radial partition immunoassay. The molecular size of the CNBr-cTnI isoform is comparable in molecular weight to the major degradation product of native cardiac TnI in MI patient serum.

It is desirable to use an immunologically reactive human cTnI isoform comparable to that detected in MI patient serum. The availability of r-TnI can facilitate the production of cardiac cTnI isoforms. Moreover, since most of the known human cardiac specific TnI antibodies have their epitopes located approximately in the first 75% of the TnI molecule, that portion of the TnI molecule will function as a cTnI isoform in most immunoassays.

The CNBr-cTnI isoform can be used as calibrators or controls in various cTnI immunoassays.

U.S. Ser. No. 98/865,468, filed May 29, 1997, discloses the use of cardiac troponin I fragments of the general sequence X-A-B-Y wherein X comprises any of amino acids 1–27 of full length cardiac troponin I, A comprises residues 28–69 of full length cardiac troponin I, B comprises amino acid residues 70–90 of full length cardiac troponin I, and Y comprises any sequential amino acid sequence of amino acid residues 91–170 of full length cardiac troponin I. These sequences also have increased immunoreactivity and stability over prior art compounds.

Troponin T (TnT) with a molecular weight of 39,000 Kd is part of the troponin-tropomyosin complex of the thin filament that is part of the muscle contractile apparatus and that contains actin and tropomyosin regulatory elements. Skeletal muscle studies of TnT have found that TnT is structurally asymmetric. Its terminal globular COOH terminal domain (TnT-2) mediates its interaction with TnI and TnC. TnT-1 at the amino terminus domain interacts with tropomyosin. See, Farah, C. and Reinach, F. (1995) Review: The Troponin complex and regulation of muscle contraction. FASEB Journal 9 755–767. It is reported that skeletal TnT is cleaved into the skeletal TnT-1 and TnT-2TnI-TnC fragments by mild proteolysis. Schaertl, S. et al. (1995) Separation and Characterization of the Two Functional Regions of Troponin Involved in Muscle Thin Filament Regulation. Biochemistry 34 (49) 15890–15894. TnT serves as a link between the tropomyosin backbone and the Troponin I/Troponin C complex. TnT has isotypes in cardiac and fast and slow skeletal muscles. It appears in serum about 3 hours after the onset of chest pain and remains elevated for at least 10 days following MI. Despite its lack of complete cardiac specificity it can be useful because of its rapid appearance into the bloodstream. Troponin T can be obtained as described in J. Biochem. 72: pages 723–735 (1972) or J. Biol. Chem. 249: 4742–4748, or purchased commercially. TnT gene promoter and derivatives thereof are disclosed in U.S. Pat. No. 5,266,488. TnT isoforms of skeletal muscle show variation in a given species in about a 30 amino acid region of the amino terminus and about a 14 amino acid region of the carboxy terminus. Pan, B. S. and Potter, J. D.(1992) Two Genetically Expressed Troponin T fragments Representing α and β Isoforms Exhibit Functional Differences. Journal of Biological Chemistry 267 (82) 23052–23056.

In vitro stabilized solutions for cardiac markers have been disclosed. U.S. Pat. No. 5,583,200 and Bodor et al., (1992) Development of Monoclonal Antibodies for an Assay of Cardiac Troponin-I and Preliminary Results in Suspected Cases of Myocardial Infarction, Clinical Chemistry 38, (11) 2203–2214 at 2204 disclose stabilized troponin T and/or troponin I using troponin C and calcium ion. U.S. Pat. No. 5,583,200 discloses that serum may be added. U.S. Ser. No. 08/874,566, filed Jun. 13, 1997, discloses improvements in stabilizing the troponin T or troponin I/troponin C complex and discloses solutions useful as calibrators or controls for diagnostic assays measuring troponin. U.S. Ser. No. 08/564,526 and U.S. Ser. No. 08/865,468, filed May 29, 1997 also disclose the effect of TnC upon the immunological and biological activity and non-specific binding of the CNBr-cTnI isoform and other fragments. U.S. Ser. No. 08/564,526 discloses the activity of the complex formed by the CNBr-cTnI isoform, TnC and TnT as useful in immunoassays.

The calibrators and controls in Behring's OPUS® assay are a lyophilized preparation of human cardiac troponin I in processed bovine calf serum with stabilizers. The reconstituted products are stable for seven days when stored at 2 to 8 C. The calibrators and controls in Sanofi Pasteur's troponin I assay are a lyophilized preparation in a buffered human serum matrix. The reconstituted calibrators must be used within fifteen minutes after complete reconstitution, but may be aliquoted and stored frozed at −20 C for up to about six months. The calibrators and controls in the Dade troponin I assay are provided frozen. When thawed the product is stable for thirty days when stored at 2–8 C.

Improved methods and compositions of stabilized troponin I and/or troponin T are still necessary because under certain conditions the complex can dissociate (e.g. removal of calcium, presence of detergents such as SDS). Moreover, the closer the analyte used in the composition is to the actual circulating isoform of the troponin complex, the better the composition will perform as a primary reference material — that is a calibrator on which other calibrators are based.

SUMMARY OF THE INVENTION

This invention relates to stabilized compositions of: troponin I and troponin C complex (TnI:TnC); troponin T and troponin C complex (TnT:TnC); troponin T and troponin I complexes (TnI:TnT) and troponin I, troponin T, and troponin C complexes (TnI:TnC:TnT) for use in immunoassay of cardiac troponins.

Troponin I and/or troponin T can be covalently complexed to troponin C to provide a composition that has enhanced stability and/or immunoreactivity over prior art complexes and analytes.

In a TnI:TnC complex, the TnI is covalently coupled to TnC. The troponin I may be native or recombinant or may be fragmented or full-length.

In a TnT:TnC complex, the TnT is covalently coupled to TnC. The TnT may be native or recombinant or may be fragmented or full-length.

In a TnT:TnI complex the TnI and TnT are covalently coupled.

In a TnT:TnC:TnI complex either or both of the TnI or TnT is covalently coupled to TnC.

The complexes are useful as calibrators or controls for methods that assay for TnI, TnC, and/or TnT or for use as primary reference materials.

The control composition should contain a buffer or serum base matrix and may contain such metal ions as calcium and/or magnesium ions. The control composition may be lyophilized or liquid.

The covalent coupling agents include those coupling agents that provide substantially "native-length" covalent cross-linking between troponin T and/or troponin I with troponin C. The term "native-length" cross-linking as used herein means a covalent bond formed between either troponin I or T with troponin C that provides a covalently coupled complex that has substantially the same immunological activity as non-covalently coupled complex. Generally the length of the covalent bond should approximate the length between troponin I and/or T with troponin C in native complex or between troponin I and troponin T in native complex. But, because protein complexes are rarely rigid in structure, it is to be understood that there is variability in the structure of the complex. The stability and immunological activity of the covalently coupled complex are what is important.

BRIEF DESCRIPTION OF THE FIGURES

FIG. 1 shows the amino acid sequence of cardiac troponin as expressed by Dade International (SEQ ID NO. 1) and of cardiac troponin I (SEQ ID NO. 2).

FIG. 2 shows the amino acid sequence of the CNBr cleavage product of recombinant troponin I (human cTnI isoform or TnI-153).

DETAILED DESCRIPTION OF THE INVENTION

Figure 3:
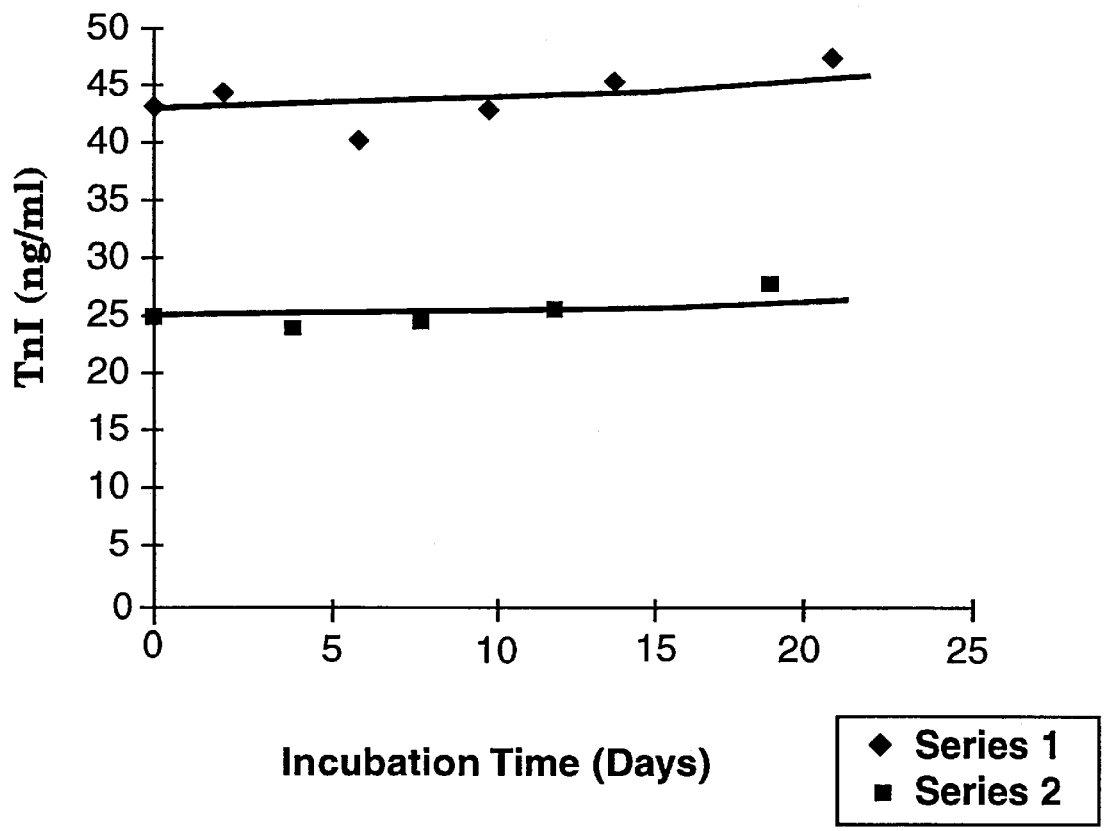
FIG. 3 shows the stability and immunoreactivity at 45 C of cross-linked rTnI-153:TnC complex at two dilutions of complex. The samples were evaluated using a Stratus II analyzer and Stratus Troponin Fluorometric Assay Kit both available from Dade International.

In a TnI:TnC complex, the TnI is covalently coupled to TnC. The cardiac troponin I may be native or recombinant and may be fragmented or full-length. While some uncomplexed troponins can be found in human serum after a myocardial event, most cardiac specific troponin is found as complex. It has been found that the TnI in the complex is degraded by proteolytic cleavage at the C-terminal end to provide an 18,000 Kd fragment and a 14,000 Kd fragment. Generally the 14,000 Kd fragment is cleaved from the 18,000 Kd fragment. After the cleavage to the 18,000 fragment, an N-terminus proteolytic cleavage occurs at the carboxyl side of Arg 26, thus eliminating the first 26 amino acids of the N-terminus. The 31 amino acid sequence at the N-terminus had been proposed as the best position to direct antibodies against, however, this recent finding suggests that those antibodies would only recognize a fraction of serum TnI.

Thus, it is preferred that the complexes of the present invention that contain cardiac troponin I contain at least a fragment of troponin I generated from the 14,000 Kd fragment. It is inherent that antibodies for use in immunoassay be generated against that portion of troponin I or troponin complex that includes the 14,000 Kd troponin I sequence. Of course, the antibody must react immunologically (e.g. have an eptitopic-site on the fragment) and specifically (e.g. it should not substantially cross react with skeletal muscle troponin I) with the cardiac troponin I or complex used in the calibrator or control.

Thus, the use of a human cTnI fragment generated from human cardiac r-TnI by chemical cleavage is a preferred fragment for the TnI:TnC complex because it is closest to the majority of the native form. The cleavage of r-TnI by cyanogen bromide (CNBr) results in a major polypeptide of 153 amino acids, hereinafter referred to as the "CNBr-cTnI isoform" (SEQ ID NO: 3). The CNBr-cTnI isoform represents 73% of the primary structure of human cTnI and is immunologically more reactive than r-TnI as determined using radial partition immunoassay. The purified CNBr-cTnI isoform has an average of 3–4 times more reactivity than r-TnI and lower non-specific binding, as measured by radial partition immunoassay, available from Dade International Inc. As demonstrated in FIG. 2 the molecular size of the CNBr-cTnI isoform is comparable in molecular weight to the major degradation product of native cardiac TnI in MI patient serum and retained the epitopes for the antibodies used in the Stratus® II TnI Immunoassay System. (See Vallins et al. (1990) FEBS Lett. 270, 57–61.)

Generally described, the first step in cyanogen bromide cleavage is to carboxymethylate the cysteine residues of r-TnI (there are two in the TnI sequence) (SEQ ID NO: 1) at positions 79 and 96 in order to prevent dimerization by inter or intra molecular disulfide bridges. The carboxymethylation of the cysteine residues is not a pre-requisite for the generation of the 153 amino acid isoform. (SEQ ID NO: 3.) Rather, the carboxymethylation facilitates the process by minimizing the complications during or after CNBr digestion.

CNBr treatment is carried out on the carboxymethylated r-TnI. Unlike other possible cleavage reactions (e.g.

enzymatic), the CNBr treatment removes the tail sequence, the leading sequence, and part of the TnI C-terminal region without affecting the primary sequence of the immunogenic sites.

Other preferred peptides are disclosed in U.S. Ser. No. 08/865,468, filed May 29, 1997 and include cardiac troponin I fragments of the general sequence X-A-B-Y wherein X comprises any of amino acids 1–27 of full length cardiac troponin I, A comprises residues 28–69 of full length cardiac troponin I, B comprises amino acid residues 70–90 of full length cardiac troponin I, and Y comprises any sequential amino acid sequence of amino acid residues 91–170 of full length cardiac troponin I.

Preferred residues for X include residues 1–27, 2–27, 3–27, 4–27, 5–27, 6–27, 7–27, 8–27, 9–27, 10–27, 15–27, 20–27, 21–27, 22–27, 23–27, 24–27, 25–27, 26–27, and 27 of SEQ ID NO: 2. More preferably, X is amino acid 27 of SEQ ID NO: 2.

A comprises amino acid residues 28–69 of SEQ ID NO: 2. B comprises amino acid residues 70–90 of SEQ ID NO: 2. Preferred residues of Y include residues 91–92, 91–93, 91–94, 91–95, 91–96, 91–97, 91–98, 91–99, 91–100, 91–105, 91–110, 91–115, 91–116, 91–117, 91–118, 91–119, 91–120, 91–121, 91–122, 91–123, 91–124, 91–125, 91–126, 91–127, 91–128 91–129, 91–130, 91–131, 91–132, 91–133, 91–134, 91–135, 91–136, 91–137, 91–138, 91–139, 91–140, 91–141, 91–142, 91–143, 91–144, 91–145, 91–146, 91–147, 91–148, 91–149, 91–150, 91–151, 91–152, 91–153, 91–154, 91–155, 91–160, 91–165, 91–170 of SEQ ID NO: 2. More preferably, Y can be any of 91–95, 91–100, 91–105, 91–110, 91–115, 91–120, 91–130, 91–140, 91–145, 91–150, 91–153, 91–155, 91–160, 91–165, 91–170 of SEQ ID NO: 2.

The lower molecular weight 14,000 TnI fragment, isolated from a pool of patient serum has been sequenced for N-terminal identification. The N-terminal sequence of the TnI 14,000 fragment starts at position 27 (Ala) in human cardiac TnI sequence. The 14,000 fragment is approximately loo amino acids long, ending in the region from about amino acid 120 to about amino acid 130 in intact cTnI. The N-terminal sequence of the 18,000 fragment starts at or very near the N-terminus of the intact human cTnI. The 18,000 fragment is approximately 140 amino acids long, ending in the region from about amino acid number 135 to about 145 in intact cTnI. Thus, one preferred group of fragments has X as 25–27, 26–27 or 27 of SEQ ID NO: 2 and Y as 91 to any of 135–145 of SEQ ID NO: 2.

The fragments also may be those cardiac troponin I protein fragments containing the sequence AYATEPHAKKKSKISASRKLQLKTLLLQIAKQEL (SEQ ID NO: 4) or RAYATEPHAKKKSKISASRKLQLK-TLLLQIAKQEL (SEQ ID NO: 5). The fragments may be recombinant sequences such as MADGSSDAAREPRPA-PAPIRRRSSNYRAYATEPHAKKKSKISASRKLQLKTL-LLQIAKQELEREAEERRGEKGRALSTRCQPLELAGL-GFAELQDLCRQLHARVDKVDEERYDIEAKVTKNITE-IADLTQKIFDLRGKFKRPTLRRVRISADAMMQALLG-ARAKESLDLRAHLKQVKKEDTEKENREVGDWRKN-IDALSGMEGRKKKKFEES (SEQ ID NO: 6); ADGSS-DAAREPRPAPAPIRRRSSNYRAYATEPHAKKKSKISA-SRKLQLKTLLLQIAKQELEREAEERRGEKGRALSTR-CQ (SEQ ID NO: 7); or similar human or bovine fragments. It should be understood that while human troponin is preferred, other species may be substituted. Generally, these other species lack the appropriate methionine residue in the full length primary structure. However, insertion of methionine into the primary structure at positions that upon cleavage by CNBr would provide an appropriate fragment would allow the use of alternative species.

Troponin C is commercially available from a number of sources and the source or species is not critical. Generally, rabbit troponin C is used because of the lower cost, but human and other species can also be used. Recombinant troponin C can also be used. The molecular weight of troponin C is about 17,500 Kd. As stated earlier, TnC has a Ca++/Mg++ binding domain in the COOH terminal region and a Ca++ binding domain in the amino terminus region and is thought to be "dumb-bell" shaped connected by a long central helix.

The covalent coupling agents useful in the present invention include those coupling agents that provide substantially "native-length" covalent cross-linking between troponin T and/or troponin I with troponin C. The preferred coupling agents form covalent bonds between the TnI or TnT and TnC that approximate the distance between the proteins as they exist in the complex. The cross-linkers may be those "zero-length" crosslinkers such as l-ethyl-3-[3-(dimethylamino) propyl]carbodiimide (EDC) and other water soluble carbodiimides providing an amide bond between an activated carboxyl group on one protein and coupling to an amino group on the other protein. See, Chemistry of Protein Conjugation and Cross-Linking, CRC Press, Inc. Other coupling agents such as oxalic, malonic and succinic acid derivatives may also be used as may many of those commercially available cross-linkers such as those available from Pierce Chemical Co. The actual coupling agent used is less important than how the covalently coupled complex performs immunologically or with regard to stability when compared to non-covalently coupled complex, native complex or commercially available products.

The complex is prepared by combining the coupling agent with troponin C and troponin I in a manner specific for the coupling agent. The coupling reaction of the TnC and TnI should take place in the presence of Ca++ or Mg++ or other divalent metal ions. The conditions will vary depending on the coupling agent utilized, but those conditions can readily be determined by those skilled in the art with reference to known and published methods. The choice of buffer is not critical, although the buffer should have a molarity from about 10 to 200 mM. The concentration of calcium and magnesium ion is not critical, but preferably should be from about 20 $\mu$M to about 20 mM. If magnesium ion is used alone it should be in higher concentrations than that used for calcium. Typical amounts of calcium and/or magnesium are from about 2–5 mM. The buffer may include a salt such as sodium chloride or potassium chloride at from about 50 mM to 500 mM. The amount of troponin C is not critical, but should be in molar amounts equal to or greater than the amount of troponin I that will be utilized. Generally, the amount of troponin C may be from 0.02 mg/mL to 5 mg/mL. The amount of coupling agent may need to be adjusted depending on the amount of troponin C.

Clinically significant concentrations of diluted final coupled product are evaluated immunologically in a troponin I assay (such as those available from Dade International Inc.) and may be compared to native complex or non-covalently coupled complex or commercially available products evaluated in the same manner. Generally the clinical range of interest of troponin I or T is about 0.01 ng/mL to less than 1 $\mu$g/mL and typically 0.1 ng/ml to 200 ng/mL. In addition, stability may be determined by comparing the immunological activity over time at one or more temperatures in comparison to native complex or non-covalently coupled complex or commercially available products evaluated in the same manner or by running electrophoretic gels of the complexes to evaluate the stability.

Native complex may be obtained in serum samples. In addition, native complex can be isolated. Methods are known to those skilled in the art. For instance, a preferred method of isolating the Tn complex comprises incubating the sample to be tested with a substrate coated with antibodies to the subunits of the Tn complex. Many antibodies are useful, and can be selected by one of skill in the art. Examples of such antibodies include anti-TnI, anti-TnC, and anti-TnT antibodies. A preferred substrate is beads, and more preferably the substrate comprises latex beads. The bound complex is eluted under conditions that do not affect association of Tn subunits, e.g. using urea. These conditions can be determined by one of skill in the art. A preferred buffer system comprises urea and lacks SDS.

A preferred coupling agent is EDC or other water soluble carbodiimides. In a buffered solution containing salt and calcium ions, troponin C is combined with EDC. The concentration of EDC is not critical and may be from 1–10 mM. Compounds such as N-hydroxysuccinimide (NHS) or SNHS at about 1–10 mM may be added to enhance the activation of troponin C by water soluble carbodiimides. The NHS is typically added prior to the addition of EDC and incubates with the protein for at least about 5 minutes, although 15 minutes is typical. Then the EDC is added and the mixture is incubated, typically at room temperature, for about 15 minutes, but typically for thirty minutes or more. The reaction proceeds best at mildly acidic pH values (e.g. about 6), but the pH may range from 5–9. After a sufficient reaction time, a reducing agent such as mercaptoethanol is added to stop the reaction. Other reducing agents may be substituted for mercaptoethanol.

Next, cardiac troponin I, preferably the CNBr-TnI isoform, is added to provide a molar ratio of about 1:1 with troponin C, although the amount of TnI may be less. TnI is generally in a buffer that contains salt or urea in sufficient amounts to solubilize the TnI. A typical buffer is 100 mM sodium phosphate, 10 mM Tris and 8 M urea at pH 8 (PTU buffer). The choice of the buffer is not critical to the invention. The buffer, however, must maintain the solubility of the cTnI. The reactants incubate, generally at room temperature, for about an hour and typically about two hours. The formed complex may be buffer exchanged into another buffer. The activity of the cross-linked complex is measured using a Stratus Troponin immunoassay and compared to native complex. The presence of the covalently cross-linked complex may be confirmed using polyacrylamide gel electrophoresis. The complex will not dissociate under reducing conditions or in the presence of EDTA or other metal complexing agent.

When using the non-specific coupling agents such as EDC, calcium or magnesium ion should be present in either the TnC or TnI solution. The calcium and/or magnesium causes complex formation to occur. Thus, the complex forms as it would in native complex so the spatial orientation of the proteins will be comparable to native complex or non-covalently coupled complex. Thus, the cross-linking occurs more selectively and the bond formed will "freeze" the complex in the correct conformation. The covalently coupled complex is insensitive to EDTA or other chelating agents (thus, independent of calcium or magnesium), does not dissociate in the presence of SDS, and is more resistant to higher temperatures than the non-cross-linked complex.

In addition, generally the TnC, rather than the TnI or TnT, should be subjected to EDC or other water soluble carbodiimide treatments. For instance, if TnI is activated by EDC without protection of the epitopic site, there is the possibility that the epitopic site would be affected by the non-specific coupling agent—that is the TnI or fragment would be less immunologically active.

The TnT:TnC complex and TnT:TnC:TnI complex are prepared in a similar fashion to the TnI:TnC. TnT fragments, particularly the carboxy fragments such as TnT-2 are preferred. As described for troponin I, the troponin T should be added in molar amounts equal to or less than the amount of troponin C. Troponin C may be from less than 0.02 mg/mL to 5 mg/mL. The ranges for TnI and TnT are similar. The TnT:TnC complex is evaluated as described for troponin I complexes, except using an assay for troponin T. Troponin T assays are available from Boehringer Mannheim.

A TnT:TnI complex may also be prepared, however, as with the other complexes of this invention, the immunological (epitopic) sites must be substantially retained. Since both TnT and TnI are measured immunologically, it is preferred that the epitopic region be retained for both proteins. Thus, less non-specific coupling agents may be useful than agents such as EDC or oxalic acid derivatives.

It has been described that skeletal muscle TnI complexes with TnT at about amino acids 40–80 of TnI. See Potter, J. D. et al. (1995) A Direct Regulatory Role of Troponin T and a Dual Role for Troponin C in the Ca++ Regulation of Muscle Control. Journal of Biological Chemistry 270 (6) 2557–2562. Thus, it is proposed that the homologous site on cTnI would be useful for coupling. Preferably, TnI and TnT are added in approximately equimolar ratios. The amounts may be from 0.02 mg/mL to 5 mg/mL. It is important that the immunological site not be altered. It should be understood that the eptitopic site will vary depending on the antibody used in the assay. The generation of antibodies is described in the art, for example, by Bodor et al., (1992) Development of Monoclonal Antibodies for an Assay of Cardiac Troponin-I and Preliminary Results in Suspected Cases of Myocardial Infarction, Clinical Chemistry 38 (11) 2203–2214. In addition, several methods that assay for troponin I or T are commercially available.

The present invention uses a defined base material useful as a control matrix for containing and maintaining the troponin complexes, the base material comprising an aqueous solution of a buffer to maintain the pH at 5–8, antimicrobial agents and may contain other stabilizers including calcium ions or proteins.

The defined base material may be utilized to prepare stock solutions and controls including troponin I or troponin I fragments, troponin T or troponin T fragments complexed with Troponin C or troponin I complexed with troponin T.

The resulting solution can be stored as a liquid or frozen or also can be lyophilized if appropriate fillers are included.

It is preferred to prepare a stock solution at higher concentrations of troponin I and/or troponin T than those that will be utilized in the final assay control. The stock can be stored frozen or lyophilized and thawed or reconstituted when necessary to prepare the appropriate dilutions of controls or calibration standards. Thus, the complexes prepared as described above may be buffer exchanged into an appropriate buffer after covalent coupling.

The aqueous solution used to prepare the stock and controls may include a buffer and the buffer may generally be any of the buffers that function in the pH range of 5 to 8. Of these buffers, the buffers that are preferred function are in the pH range of 6–8. The concentration of buffer is between 10 mM to 200 mM. It is preferred to keep the buffer concentration lower—in the range of 20–100 mM. Preferably, the buffers used for the calibrators or controls contain bovine serum albumin (BSA). In certain embodiments the buffer contains, BSA, sugars, salt and an antibacterial agent. Examples of useful buffers include HEPS, MES or TRIS buffers. A preferred buffer comprises MES buffer containing 6.5% BSA, at pH 6–7. Other preferred buffers contain a reducing agent, stabilizing protein, chelating agent and a salt as described in the copending application U.S. Ser. No. 08/400,158, incorporated herein by reference.

Alternatively, instead of a buffer, the fragments are spiked into the serum, e.g., human or bovine, or into diluted serum, e.g., serum diluted 1:1 with MES buffer containing BSA.

Anti-microbial and anti-fungal agents may be added to prevent growth and may include those commonly found in the prior art at the concentrations found in the prior art such as gentamycin, clortrimazole, sodium azide, mycostatin, thimerosal, Kathon and/or Proclin 300.

In addition, stabilizing proteins such as albumin, gelatin, ovalalbumin, or casein may be included. The concentration of stabilizing protein may be from 0 to 15% and preferably from 7 to 12%. Preferably the stabilizing protein is albumin and preferably the albumin is substantially protease free.

It is preferred that the solution have low protease activity, thus protease inhibitors such as aprotinin and "Protease Inhibitor" (Sigma) are effective. However, the use of the recombinant fragments as described herein are not as sensitive to protease activity as is the full length protein. The inhibitors may be added and may be used at the manufacturer's recommended concentration.

Examples of other protease inhibitors include benzamidine, (2S, 3R)-3-Amino-2-hydroxy-5-methylhexanoyl]-Val-Val-Asp (Amastatin-Sigma), [2S,3R]-3-Amino-2-hydroxy-4-[4-nitrophenyl]-butanoyl-L-leucine, Antipain, [2S,3R]-3-Amino-2-hydroxy-5-methylhexanoyl]-Val-Val-Asp (Epiamastatin-Sigma), ([2R,3R]-3-Amino-2-hydroxy-4-phenylbutanoyl)-L-leucine (Epibestatin-Sigma), Foroxymithine, Acetyl-Leu-Leu-Arg-al (Leupeptin-Sigma), 4-Amino-3-hydroxy-6-methyl-heptanoic acid, 4-Amino-3-hydroxy-6-methylheptanoic acid, N-($\alpha$-Rhamnopyranosyloxy-hydroxyphosphinyl)-Leu-Trp and phenyl methane sulfonyl fluoride (PMSF). It is most preferred that the means to provide a substantially protease free solution is to use substantially protease free proteins such as albumin which is substantially protease free.

Serum may be included if desired. Again, the use of fragments that are similar to the 14,000 Kd fragments substantially eliminates the concerns of proteases.

Controls prepared by this method may be lyophilized by adding those bulking agents that are known in the art, but the controls may also be liquid. In addition, the liquid controls may be frozen to further increase shelf-life.

Currently used assays for detecting cTnI and cTnT in MI patient serum utilize a sandwich assay. However, the complexes of the present invention can also be used to design competitive-type assays for the detection of cTnI or cTnT in serum. In such an assay, a subsaturating amount of antibody to cTnI or cTnT is bound to a solid phase, e.g., a microtiter plate or latex beads. The complexes of the present invention are labeled, e.g., with alkaline phosphatase, or horseradish peroxidase. A constant amount of the labeled complex is mixed with the sample of MI patient serum containing an unknown amount of cTnI and/or cTnT. The test sample is then allowed to bind to the subsaturating amount of cTnI and/or cTnT antibody bound to a solid phase. The cTnI and/or cTnT in the sample will compete with the labeled complex for binding with the antibody-coated solid phase. Unbound proteins are removed by washing and the amount of labeled complex bound to the solid phase is measured. The amount of labeled complex bound to the antibody on the solid phase indicates the amount of cTnI or cTnT present in the serum. If the serum contains a high concentration of cTnI or cTnT, it will compete effectively with the labeled complex and little or none of the labeled complex will bind the antibody-coated solid phase.

Changes in some amino acids of the fragments of TnI, TnT, and TnC might not affect their performance except those occurring at the epitope(s) where the specific assay antibodies bind and those amino acids of the binding domains for TnC. The affects can readily be determined by gel electrophoresis and immunological analysis of prepared complex.

EXAMPLE 1

Preparation of a Defined Base Material for Cardiac Markers.

Antioxidants such as 200 milligrams of glutathione, 200 milligrams of glucose, 50 mgs of ascorbic acid, and 1.1 milliliter of phenol, about 2.7 grams of L-Lactate, about 225 milligrams of calcium chloride or other calcium salt to provide 1–3 mM calcium ion, anti-microbial and anti-fungal agents such as about 20 milligrams of chlortrimazole, 35 milligrams of gentamicin, and about 1 milliliter of Proclin 300, about 95 grams of protease free BSA, and about 1 gram of gelatin are combined in an aqueous 50 mM TRIS buffered solution at about pH 7.3 also containing a salt such as sodium chloride (about 30 grams) to provide about one liter of base material.

It is best to add the gelatin in solution by dissolving the gelatin by adding 1 gram of gelatin to 100 milliliters of water and gently heating to dissolve the gelatin. Then the gelatin containing solution is added to the base material.

The resulting solution is filtered using filters sufficient to remove any bacteria such as a 0.22 micron filter. A low protein binding filter is preferred.

EXAMPLE 2

Cross-Linking of Troponin I and Troponin T Preparation of Troponin I Stock Solution and Controls.

The cross-linking was accomplished using the EDC method described by Greaser and Gergely (1971). To 20 mM Mes buffer at pH 6 containing 0.1 M KCl, 0.2 mM $CaCl_2$, freshly prepared NHS at 5.7 mM final concentration was added followed by addition of TnC to provide 0.2 mg/mL. The mixture was incubated at room temperature for 15 minutes. The TnC was activated by addition of 5.7 -mM EDC (final concentration) followed by incubation at room temperature for 30 minutes. The activation step was terminated by addition of β mercaptoethanol (20 mM final concentration). The CNBr-rTnI isoform (TnI 153) in PTU buffer was added at a final concentration of 0.175 mg/mL. The mixture was incubated for two hours at room temperature. The complex is buffer exchanged. The activity of the crossed linked complex was measured using Stratus TnI immunoassay. The presence of a covalent cross-linked complex was confirmed on polyacrylamide gel electrophoresis. The resulting complex is less sensitive to environment, including temperature than native complex. The resulting stock solution is sterile filtered using low protein binding filters of 0.22 microns or less. The stock solution may be stored frozen at −20° C. for longer than two years. The stock solution may be stored at 2–8° C. for more than one week.

The stock solution is used to prepare diluted solutions of troponin I in the clinical range of interest (about 0 to 200 ng/mL) by diluting the stock solution in the defined base material prepared in Example 1 or other base material.

EXAMPLE 3

Stability and Immunological Activity of the Covalently Coupled Complex.

Figure 4:
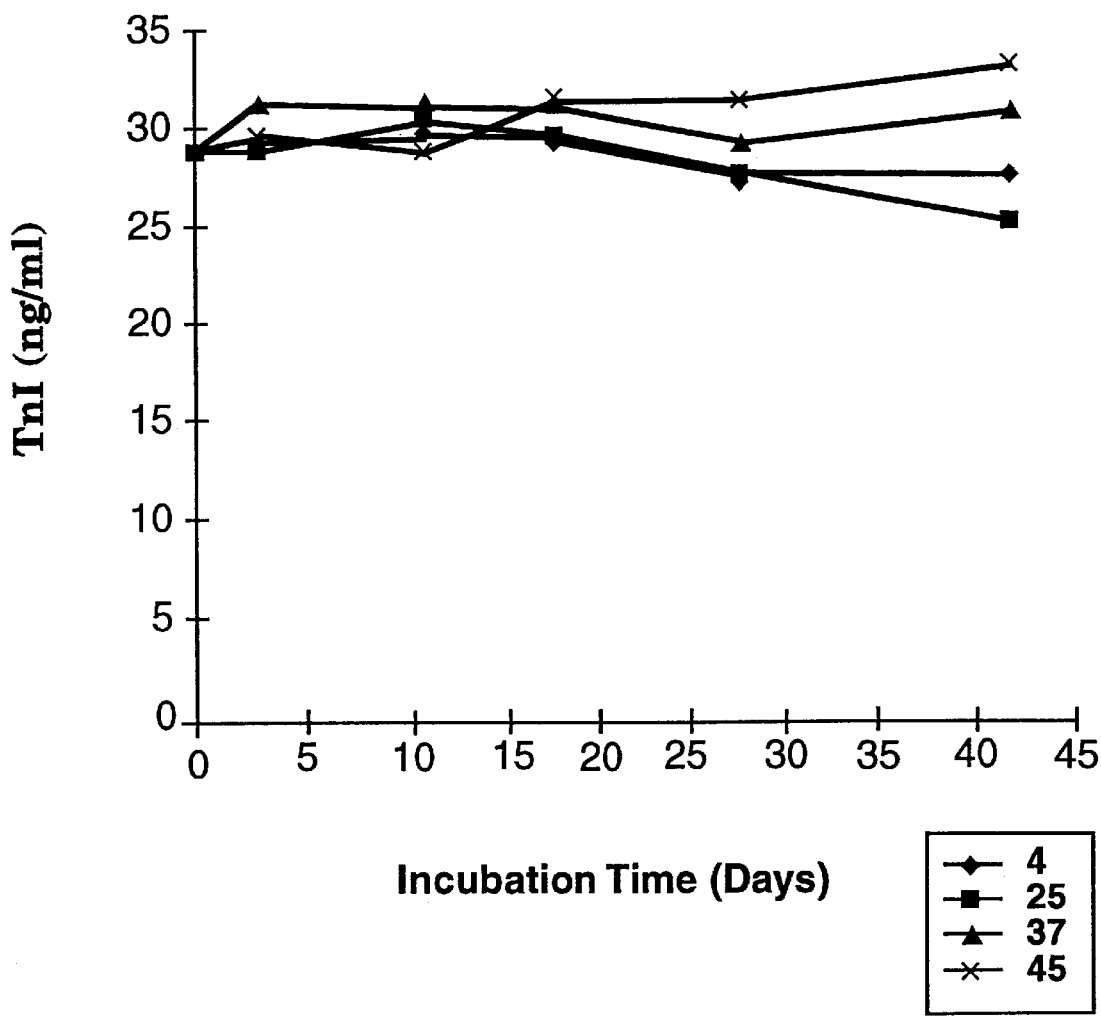
FIG. 4 shows the stability at different temperatures of diluted cross-linked rTnI-153:TnC complex. The samples were evaluated using a Stratus II analyzer and Stratus Troponin Fluorometric Assay Kit both available from Dade International.
Figure 5:
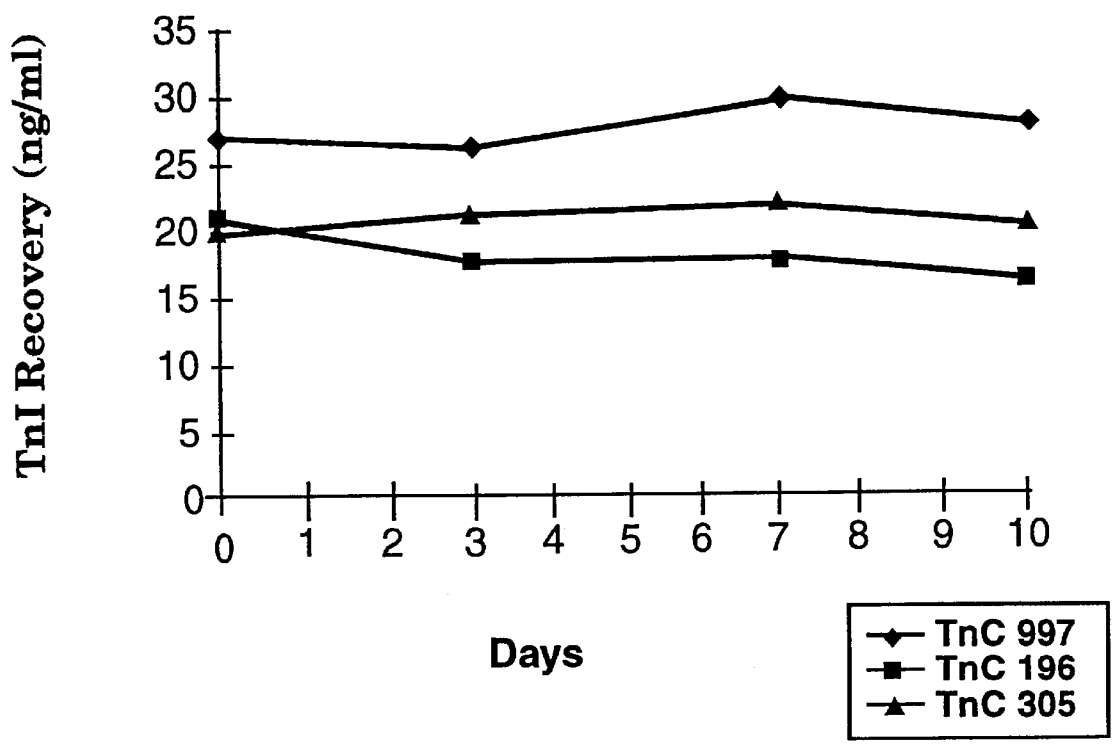
FIG. 5 shows the stability of the cross-linked rTnI-153:TnC complex using three different lots of TnC.
Figure 6:
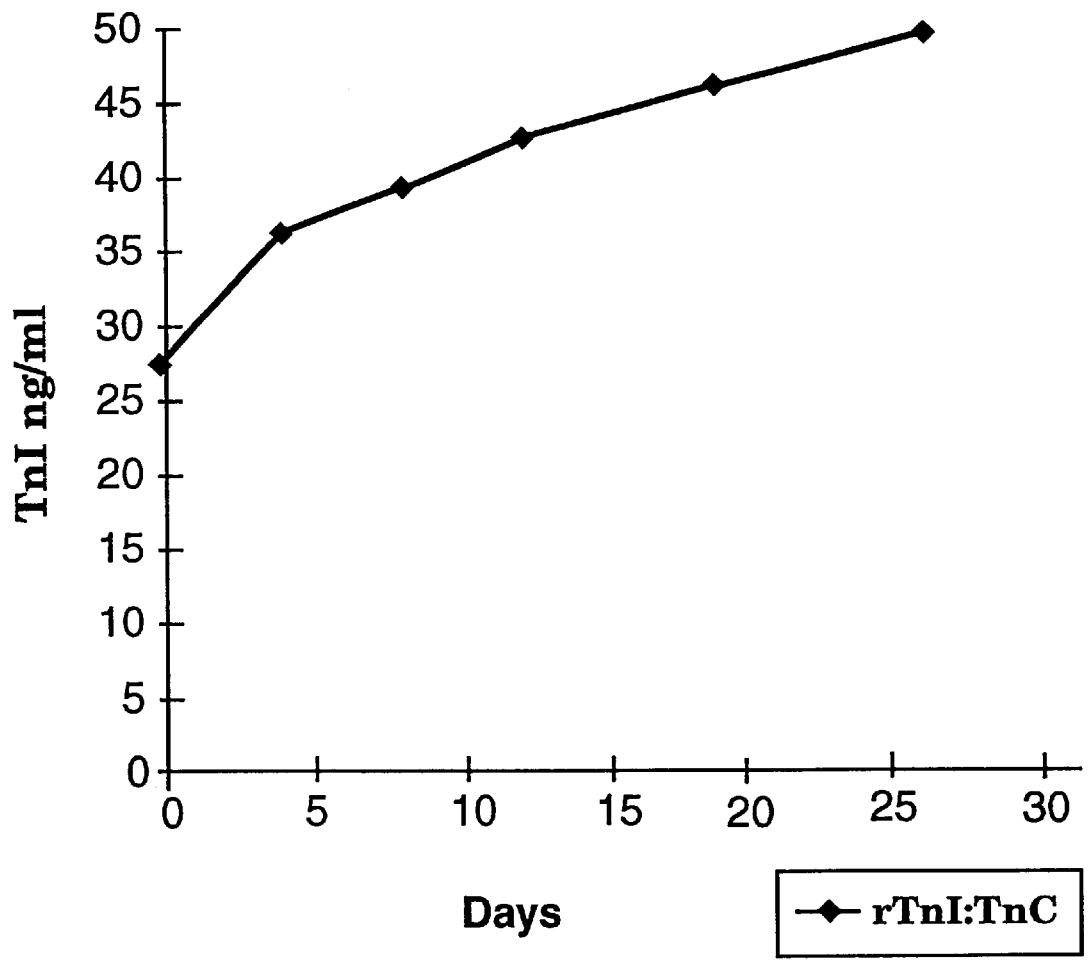
FIG. 6 shows the stability of cross-linked rTnI:TnC complex at 45 C.

Various aliquots representing different concentrations of troponin I complex prepared in Example 2 (of the diluted stock solution) were stored at various temperatures. The aliquots were analyzed on a Stratus II Immunoassay analyzer for troponin I concentration. The change in concentration was evaluated over time. FIG. 3 shows the stability of two concentrations of diluted stock (25 ng/mL and 45 ng/mL of troponin I) of the complex stored at 45 C. The dilutions are stable for greater than three weeks at 45 C. FIG. 4 shows a 28 ng/mL solution was evaluated for stability at 4 C, 25 C, 37 C, and 45 C and was stable for at least six weeks at all temperatures. FIG. 5 shows the stability of the complex when prepared with three different lot numbers of commercially available TnC. All lots were stable for over 10 days at 45 C. A full length rTnI-TnC complex was also prepared. The stability of the cross-linked complex at 45 C is shown in FIG. 6.

EXAMPLE 4

Independence of the Complex on Calcium Ion.

Figure 7:
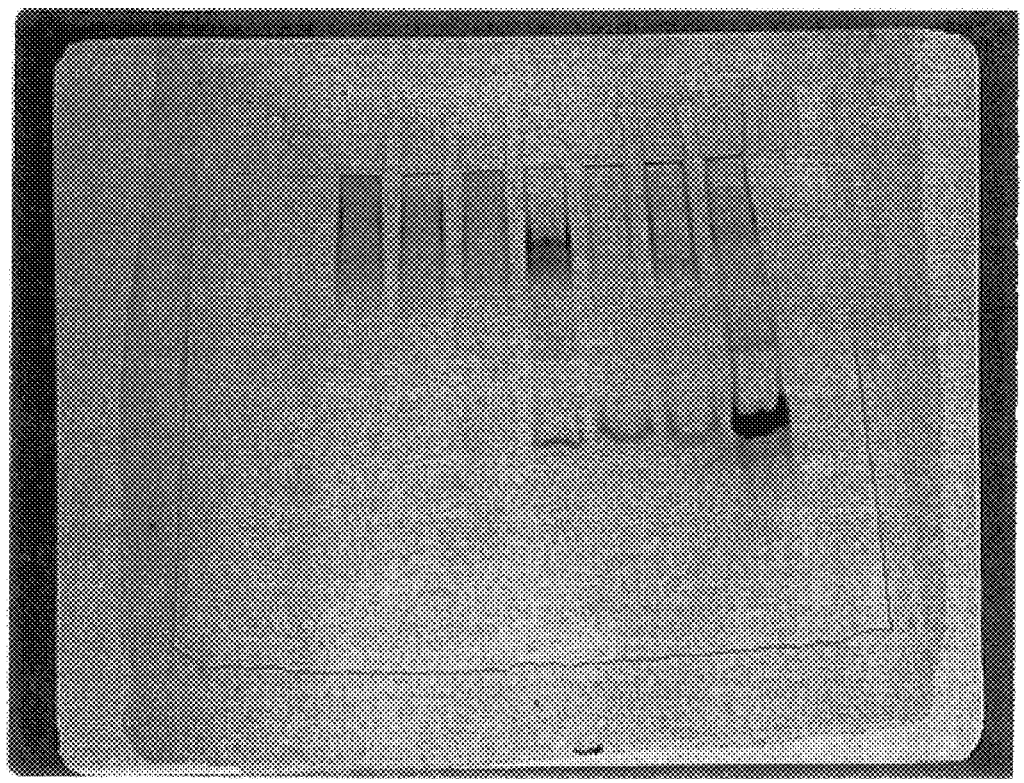
FIG. 7 shows polyacrylamide gels of cross-linked and non-crosslinked complexes of rTnI-153:TnC.

Polyacrylamide gels of the complexes were evaluated. Lanes 2–4 show the electrophoretic pattern of covalently linked rTnI-153:TnC complex in the presence of EDTA (a metal chelator). Lane 5 shows a non covalently linked rTnI-153:TnC complex in the absence of EDTA. Lanes 6–7 show he electrophoretic pattern of non covalently linked rTnI-153:TnC complex in the presence of EDTA. The disappearance of the upper band of complex is evident in Lanes 6–7, but not in Lanes 2–4. Lane 8 is TnC. See, FIG. 7.

EXAMPLE 5

Preparation of Troponin T Controls.

Example 2 is repeated except that troponin T is substituted for the troponin I. Aliquots of stock solution are diluted to the clinical range of interest from 0.01 ng/mL to 10 ng/mL. The aliquots may be analyzed for immunological activity using a troponin T assay such as that assay commercially available from Boehringer Mannheim.

EXAMPLE 6

Preparation of a Ternary Complex of Troponin I, Troponin C and Troponin T.

Example 2 is repeated except that both troponin I and troponin T are added to the activated troponin C. The ternary complex may be observed using electrophoresis run in the presence of EDTA. The troponin I immunological activity may be evaluated as described in Example 2 and the troponin T immunological activity may be evaluated as described in Example 5.

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 226 amino acids
      (B) TYPE: amino acid
      (C) STRANDEDNESS: single
      (D) TOPOLOGY: linear (xi) SEQUENCE DESCRIPTION: SEQ ID NO:1:

```
Met Ala Ser Met Thr Leu Trp Met Ala Asp Gly Ser Ser Asp Ala Ala
1               5                   10                  15

Arg Glu Pro Arg Pro Ala Pro Ala Pro Ile Arg Arg Arg Ser Ser Asn
                20                  25                  30

Tyr Arg Ala Tyr Ala Thr Glu Pro His Ala Lys Lys Lys Ser Lys Ile
            35                  40                  45

Ser Ala Ser Arg Lys Leu Gln Leu Lys Thr Leu Leu Leu Gln Ile Ala
        50                  55                  60

Lys Gln Glu Leu Glu Arg Glu Ala Glu Glu Arg Arg Gly Glu Lys Gly
65                  70                  75                  80

Arg Ala Leu Ser Thr Arg Cys Gln Pro Leu Glu Leu Thr Gly Leu Gly
                85                  90                  95

Phe Ala Glu Leu Gln Asp Leu Cys Arg Gln Leu His Ala Arg Val Asp
            100                 105                 110

Lys Val Asp Glu Glu Arg Tyr Asp Ile Glu Ala Lys Val Thr Lys Asn
        115                 120                 125
```

```
Ile Thr Glu Ile Ala Asp Leu Thr Gln Lys Ile Phe Asp Leu Arg Gly
        130                 135                 140

Lys Phe Lys Arg Pro Thr Leu Arg Arg Val Arg Ile Ser Ala Asp Ala
145                 150                 155                 160

Met Met Gln Ala Leu Leu Gly Ala Arg Ala Lys Glu Ser Leu Asp Leu
                165                 170                 175

Arg Ala His Leu Lys Gln Val Lys Lys Glu Asp Thr Glu Lys Glu Asn
                180                 185                 190

Arg Glu Val Gly Asp Trp Arg Lys Asn Ile Asp Ala Leu Ser Gly Met
            195                 200                 205

Glu Gly Arg Lys Lys Lys Phe Glu Ser Pro Met Val His His His His
    210                 215                 220

His His
225

(2) INFORMATION FOR SEQ ID NO:2:

(i) SEQUENCE CHARACTERISTICS:
        (A) LENGTH: 209 amino acids
        (B) TYPE: amino acid
        (C) STRANDEDNESS: single
        (D) TOPOLOGY: linear (xi) SEQUENCE DESCRIPTION: SEQ ID NO:2:

Ala Asp Gly Ser Ser Asp Ala Ala Arg Glu Pro Arg Pro Ala Pro Ala
1               5                   10                  15

Pro Ile Arg Arg Arg Ser Ser Asn Tyr Arg Ala Tyr Ala Thr Glu Pro
                20                  25                  30

His Ala Lys Lys Lys Ser Lys Ile Ser Ala Ser Arg Lys Leu Gln Leu
                35                  40                  45

Lys Thr Leu Leu Leu Gln Ile Ala Lys Gln Glu Leu Glu Arg Glu Ala
    50                  55                  60

Glu Glu Arg Arg Gly Glu Lys Gly Arg Ala Leu Ser Thr Arg Cys Gln
65                  70                  75                  80

Pro Leu Glu Leu Thr Gly Leu Gly Phe Ala Glu Leu Gln Asp Leu Cys
                85                  90                  95

Arg Gln Leu His Ala Arg Val Asp Lys Val Asp Glu Glu Arg Tyr Asp
                100                 105                 110

Ile Glu Ala Lys Val Thr Lys Asn Ile Thr Glu Ile Ala Asp Leu Thr
                115                 120                 125

Gln Lys Ile Phe Asp Leu Arg Gly Lys Phe Lys Arg Pro Thr Leu Arg
    130                 135                 140

Arg Val Arg Ile Ser Ala Asp Ala Met Met Gln Ala Leu Leu Gly Ala
145                 150                 155                 160

Arg Ala Lys Glu Ser Leu Asp Leu Arg Ala His Leu Lys Gln Val Lys
                165                 170                 175

Lys Glu Asp Thr Glu Lys Glu Asn Arg Glu Val Gly Asp Trp Arg Lys
                180                 185                 190

Asn Ile Asp Ala Leu Ser Gly Met Glu Gly Arg Lys Lys Lys Phe Glu
                195                 200                 205

Ser (2) INFORMATION FOR SEQ ID NO:3:

(i) SEQUENCE CHARACTERISTICS:
        (A) LENGTH: 153 amino acids
        (B) TYPE: amino acid
```

```
        (C) STRANDEDNESS: single
        (D) TOPOLOGY: linear (xi) SEQUENCE DESCRIPTION: SEQ ID NO:3:

Ala Asp Gly Ser Ser Asp Ala Ala Arg Glu Pro Arg Pro Ala Pro Ala
1               5                   10                  15

Pro Ile Arg Arg Arg Ser Ser Asn Tyr Arg Ala Tyr Ala Thr Glu Pro
            20                  25                  30

His Ala Lys Lys Lys Ser Lys Ile Ser Ala Ser Arg Lys Leu Gln Leu
        35                  40                  45

Lys Thr Leu Leu Leu Gln Ile Ala Lys Gln Glu Leu Glu Arg Glu Ala
    50                  55                  60

Glu Glu Arg Arg Gly Glu Lys Gly Arg Ala Leu Ser Thr Arg Cys Gln
65                  70                  75                  80

Pro Leu Glu Leu Thr Gly Leu Gly Phe Ala Glu Leu Gln Asp Leu Cys
                85                  90                  95

Arg Gln Leu His Ala Arg Val Asp Lys Val Asp Glu Glu Arg Tyr Asp
                100                 105                 110

Ile Glu Ala Lys Val Thr Lys Asn Ile Thr Glu Ile Ala Asp Leu Thr
            115                 120                 125

Gln Lys Ile Phe Asp Leu Arg Gly Lys Phe Lys Arg Pro Thr Leu Arg
        130                 135                 140

Arg Val Arg Ile Ser Ala Asp Ala Met
145                 150

(2) INFORMATION FOR SEQ ID NO:4:

(i) SEQUENCE CHARACTERISTICS:
        (A) LENGTH: 34 amino acids
        (B) TYPE: amino acid
        (C) STRANDEDNESS: single
        (D) TOPOLOGY: linear (xi) SEQUENCE DESCRIPTION: SEQ ID NO:4:

Ala Tyr Ala Thr Glu Pro His Ala Lys Lys Lys Ser Lys Ile Ser Ala
1               5                   10                  15

Ser Arg Lys Leu Gln Leu Lys Thr Leu Leu Leu Gln Ile Ala Lys Gln
            20                  25                  30

Glu Leu (2) INFORMATION FOR SEQ ID NO:5:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO:5:

Arg Ala Tyr Ala Thr Glu Pro His Ala Lys Lys Lys Ser Lys Ile Ser
1               5                   10                  15

Ala Ser Arg Lys Leu Gln Leu Lys Thr Leu Leu Leu Gln Ile Ala Lys
            20                  25                  30

Gln Glu Leu
        35
```

```
(2) INFORMATION FOR SEQ ID NO:6:

(i) SEQUENCE CHARACTERISTICS:
        (A) LENGTH: 211 amino acids
        (B) TYPE: amino acid
        (C) STRANDEDNESS: single
        (D) TOPOLOGY: linear (xi) SEQUENCE DESCRIPTION: SEQ ID NO:6:

Met Ala Asp Gly Ser Ser Asp Ala Ala Arg Glu Pro Arg Pro Ala Pro
1               5                   10                  15

Ala Pro Ile Arg Arg Arg Ser Ser Asn Tyr Arg Ala Tyr Ala Thr Glu
            20                  25                  30

Pro His Ala Lys Lys Lys Ser Lys Ile Ser Ala Ser Arg Lys Leu Gln
            35                  40                  45

Leu Lys Thr Leu Leu Leu Gln Ile Ala Lys Gln Glu Leu Glu Arg Glu
        50                  55                  60

Ala Glu Glu Arg Arg Gly Glu Lys Gly Arg Ala Leu Ser Thr Arg Cys
65                  70                  75                  80

Gln Pro Leu Glu Leu Ala Gly Leu Gly Phe Ala Glu Leu Gln Asp Leu
                85                  90                  95

Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
            115                 120                 125

Thr Gln Lys Ile Phe Asp Leu Arg Gly Lys Phe Lys Arg Pro Thr Leu
        130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Lys
            195                 200                 205

Phe Glu Ser
    210

(2) INFORMATION FOR SEQ ID NO:7:

(i) SEQUENCE CHARACTERISTICS:
        (A) LENGTH: 80 amino acids
        (B) TYPE: amino acid
        (C) STRANDEDNESS: single
        (D) TOPOLOGY: linear (xi) SEQUENCE DESCRIPTION: SEQ ID NO:7:

Ala Asp Gly Ser Ser Asp Ala Ala Arg Glu Pro Arg Pro Ala Pro Ala
1               5                   10                  15

Pro Ile Arg Arg Arg Ser Ser Asn Tyr Arg Ala Tyr Ala Thr Glu Pro
            20                  25                  30

His Ala Lys Lys Lys Ser Lys Ile Ser Ala Ser Arg Lys Leu Gln Leu
            35                  40                  45

Lys Thr Leu Leu Leu Gln Ile Ala Lys Gln Glu Leu Glu Arg Glu Ala
        50                  55                  60

Glu Glu Arg Arg Gly Glu Lys Gly Arg Ala Leu Ser Thr Arg Cys Glx
65                  70                  75                  80
```

What is claimed is:

1. A composition for use in an assay for the determination of the presence or concentration of cardiac troponin T or cardiac troponin I, the composition comprising: a complex of cardiac troponin T or a fragment thereof, cardiac troponin I or a fragment thereof and troponin C or a fragment thereof wherein the cardiac troponin T and cardiac troponin I are covalently coupled to the troponin C and wherein the cardiac troponin I is a fragment having substantially the amino acid sequence of a CNBr fragment designated rTnI-153.

2. A composition for use in an assay for the determination of the presence or concentration of cardiac troponin T or cardiac troponin I the composition comprising: a complex of cardiac troponin T or a fragment thereof, cardiac troponin I or a fragment thereof and troponin C or a fragment thereof wherein the cardiac troponin T and cardiac troponin I are is covalently coupled to the troponin C and wherein the cardiac troponin I is a fragment of the general sequence X-A-B-Y wherein X comprises any of amino acids 1–27 of full length cardiac troponin I, A comprises residues 28–69 of full length cardiac troponin I, B comprises amino acid residue 70–90 of full length troponin I and Y comprises any sequential amino acid sequence of amino acid residues 91–170 of full length cardiac troponin I.

3. A composition for use in an assay for the determination of the presence or concentration of cardiac troponin I, the composition comprising: a complex of cardiac troponin I or a fragment thereof and troponin C or a fragment thereof wherein the cardiac troponin I is covalently coupled to the troponin C and wherein the cardiac troponin I is a fragment having substantially the amino acid sequence of a CNBr fragment designated rTnI-153.

4. The composition of claim 3 wherein the composition is provided as a diagnostic calibrator, control or reference material for cardiac troponin I determination.

5. The composition of claim 3 wherein the cardiac troponin I and the troponin C are covalently coupled using a water soluble carbodiimide.

6. The composition of claim 3 wherein the cardiac troponin I is recombinant.

7. A composition for use in an assay for the determination of the presence or concentration of cardiac troponin I, the composition comprising: a complex of cardiac troponin I or a fragment thereof and troponin C or a fragment thereof wherein the cardiac troponin I is covalently coupled to the troponin C and wherein the cardiac troponin I is a fragment of the general sequence X-A-B-Y wherein X comprises any of amino acids 1–27 of full length cardiac troponin I, A comprises residues 28–69 of full length cardiac troponin I, B comprises amino acid residue 70–90 of full length troponin I and Y comprises any sequential amino acid sequence of amino acid residues 91–170 of full length cardiac troponin I.

* * * * *

UNITED STATES PATENT AND TRADEMARK OFFICE
CERTIFICATE OF CORRECTION

PATENT NO.    : 6,269,481 B1
DATED         : July 31, 2001
INVENTOR(S)   : Stephen G. Perlman and Tim Bucher It is certified that error appears in the above-identified patent and that said Letters Patent is hereby corrected as shown below:

Column 1,
Line 24, before "personal" change "Modem" to -- Modern --

Column 4,
Line 45, before "data" change "bidirectional" to -- bi-directional --

Signed and Sealed this

Twenty-first Day of May, 2002

*Attest:*

*Attesting Officer*

JAMES E. ROGAN
*Director of the United States Patent and Trademark Office*